US008329229B2

(12) United States Patent
Gonzalez et al.

(10) Patent No.: US 8,329,229 B2
(45) Date of Patent: Dec. 11, 2012

(54) STEAM DISTILLATION OF CATMINT PLANTS

(75) Inventors: Yamaira Gonzalez, Newark, DE (US); Scott Christopher Jackson, Wilmington, DE (US); Leo Ernest Manzer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 425 days.

(21) Appl. No.: 12/519,588

(22) PCT Filed: Dec. 20, 2007

(86) PCT No.: PCT/US2007/025997
§ 371 (c)(1), (2), (4) Date: Jun. 17, 2009

(87) PCT Pub. No.: WO2008/079261
PCT Pub. Date: Jul. 3, 2008

(65) Prior Publication Data

US 2010/0034906 A1 Feb. 11, 2010

Related U.S. Application Data

(60) Provisional application No. 60/876,556, filed on Dec. 21, 2006.

(51) Int. Cl.
*A61K 36/00* (2006.01)

(52) U.S. Cl. ........................................................ 424/725

(58) Field of Classification Search ........................ None
See application file for complete search history.

(56) References Cited

U.S. PATENT DOCUMENTS

| | | | | |
|---|---|---|---|---|
| 4,062,937 | A | 12/1977 | Rea | |
| 4,416,881 | A | 11/1983 | McGovern | |
| 4,496,467 | A | 1/1985 | Munteanu | |
| 4,869,896 | A | 9/1989 | Coulston | |
| 4,913,893 | A | 4/1990 | Varco | |
| 6,462,015 | B1 | 10/2002 | Weiss | |
| 6,524,605 | B1 | 2/2003 | Coats | |
| 6,673,756 | B2 | 1/2004 | Sonnenberg | |
| 7,067,677 | B2 * | 6/2006 | Manzer | 549/283 |
| 7,067,678 | B2 * | 6/2006 | Scialdone | 549/283 |
| 7,232,844 | B2 | 6/2007 | Hallahan | |
| 7,547,793 | B2 * | 6/2009 | Hallahan et al. | 549/283 |
| 7,820,145 | B2 | 10/2010 | Tamarkin | |
| 2004/0024054 | A1 | 2/2004 | Haenke | |
| 2005/0244441 | A1 | 11/2005 | Courtois | |
| 2006/0121134 | A1 * | 6/2006 | Chauhan et al. | 424/745 |
| 2006/0223878 | A1 | 10/2006 | Scialdone | |
| 2007/0077262 | A1 | 4/2007 | Scialdone | |
| 2007/0264297 | A1 | 11/2007 | Scialdone | |
| 2008/0305135 | A1 | 12/2008 | Kroepke | |
| 2010/0034906 | A1 | 2/2010 | Gonzalez | |
| 2010/0092404 | A1 | 4/2010 | Hutchenson | |
| 2010/0145077 | A1 * | 6/2010 | Jackson et al. | 549/283 |
| 2010/0145078 | A1 | 6/2010 | Fisher | |
| 2010/0168447 | A1 | 7/2010 | Hutchenson | |
| 2010/0261915 | A1 | 10/2010 | Gonzalez | |

FOREIGN PATENT DOCUMENTS

| | | | |
|---|---|---|---|
| WO | 03062357 | A1 | 7/2003 |

OTHER PUBLICATIONS

Regnier, Studies on the Composition of the Essential Oils of Three Nepeta Species, Phytochemistry, 1967, vol. 6, pp. 1281 to 1289.

Perry's Chemical Engineers' Handbook, 6th Edition, 1984 (Book Not Included).

International Critical Tables of Numerical Data, Physics, Chemistry and Technology, 1st Electronic Edition, Knovel Company, 2003 (Book Not Included).

International Search Report, PCT/US2007/025997, Dated May 30, 2008.

Baranauskiene et al., Sensory and Instrumental Evaluation of Catnip Aroma, J. Agric Food Chem, 2003, vol. 51, pp. 3840 to 3848.

Dapkevicius, Antioxidant Activity of Extracts Obtained by Different Isolation Procedures From Some Aromatic Herbs Grown in Lithuania, J. Sci Food and Agric., 1998, vol. 77, pp. 140-146.

Tanimori Et. Al., Total Synthesis of (+) Dihydronepetalactone, Agric. Biol. Chem., 1991,vol. 55;1181-11832.

Fleming Et. Al., Sterocontrol in Organic Synthesis Using Silicon-Containing Compounds, A Synthesis of (+) Dihydronepetalactone Using The Se2 Reacton of an Allysilane, J. Chem. Soc., Perkin Trans, 1998, vol. 1:2645-2649.

Wolinsky Et. Al., Syntheses of the Dihydronepetalactones, J. Org. Chem., 1972, vol. 37:3376-3378.

Jefson Et. Al., Chemical Defense Of a Rove Bettle, Journal of Chemical Ecology, 1983, vol. 9:150-180.

G.W.K. Cavill Et. Al., Defensive and Other Secretions of the Australian Cocktail Ant. Iridomyrmex Nitidiceps, Tetrahedron, 1982, vol. 38:1931-1938.

Chris Peterson Et. Al., Insect Repellents—Past, Present and Future, Pesticide Outlook, Aug. 2001.

Depooter Et. Al., The Essential Oils Five Nepeta Species. A Preliminary Evaluation of Their Use in Chemotaxonomy by Cluster Analysis, Flavour and Fragrance Journal, 1988, vol. 3:155-159.

Handjieva Et. Al., Constituents of Essential Oils From Nepeta Cataria L., N. Grandiflora M.B. and N. Nuda L., J. Essential Oil Res., 1996, vol. 8:639-643.

Regnier Et Al, Nepetalactone and Eipnepetalactone From Nepeta Cataria L., Phytochemistry, 1967, vol. 6:1271-1280.

T. Eisner, Science, 1964, vol. 146:1318-1320.

* cited by examiner

*Primary Examiner* — Christopher R. Tate

(57) ABSTRACT

This invention provides processes for improved recovery of essential oil from the catmint (catnip) plant *Nepeta cataria.*

18 Claims, 5 Drawing Sheets

STEAM DISTILLATION OF CATMINT PLANTS

This application claims the benefit of U.S. Provisional Application No. 60/876,556, filed 21 Dec. 2006, which is incorporated in its entirety as a part hereof for all purposes.

TECHNICAL FIELD

The present invention provides processes for improved recovery of essential oils from the catmint (catnip) plant *Nepeta cataria*.

BACKGROUND

It has been recently demonstrated that dihydronepetalactone exhibits insect repellency (see, for example, U.S. Ser. No. 05/112,166). Dihydronepetalactone can be obtained from the essential oil of the catmint plant, *Nepeta cataria*. Essential oil from *N. cataria*, herein referred to as catmint oil, has been obtained by various isolation processes, including steam distillation, organic solvent extraction, microwave-assisted organic solvent extraction, supercritical fluid extraction, mechanical extraction and enfleurage (initial cold extraction into fats followed by organic solvent extraction). Steam distillation [such as described by Regnier, F. E. et al, *Phytochemistry* (1967) 6:1281-1289] is the most economically viable method for obtaining catmint oil.

Yields of catmint oil obtained using standard distillation techniques are likely insufficient, however, for commercial production of the insect repellent dihydronepetalactone as derived from catmint oil. A need thus remains for improved techniques for the recovery of catmint oil from catmint plants.

SUMMARY

In one embodiment, the processes of this invention provide a process for obtaining catmint oil from *Nepeta cataria* by (a) contacting *Nepeta cataria* plant material with steam to form a volatilized mixture comprising catmint oil and water; (b) condensing the volatilized mixture formed in step (a) to form a liquid mixture comprising catmint oil and water in which catmint oil is dissolved in water; (c) contacting the liquid mixture formed in step (b) with salt to provide a mixture in which catmint oil and salt are both dissolved in water, and in which

- (i) the solubility of catmint oil in the solution of water and salt is at least about 50% less than the solubility of catmint oil in water, and/or
- (ii) the ratio $[(\rho_{catmint\ oil}-\rho_{aqueous\ solution})/\mu_{aqueous\ solution}]$, where $\rho$ is density, $\mu$ is viscosity and the aqueous solution is the solution of water and salt, is less than or equal to about −0.05, to provide in the mixture a catmint oil phase that is separated from an aqueous salt solution phase; and (d) recovering the catmint oil phase.

In another embodiment, the processes of this invention provide a process for obtaining catmint oil from *Nepeta cataria* by (a) contacting *Nepeta cataria* plant material with steam in a direct fired retort to form a volatilized mixture comprising catmint oil and water; (b) condensing the volatilized mixture formed in step (a) to form a liquid mixture comprising catmint oil and water; (c) separating the liquid mixture formed in step (b) into a catmint oil phase and a water phase; (d) recycling the water phase back to the direct fired retort of step (a); and (e) recovering the catmint oil phase.

In a further embodiment, the processes of this invention provide a process for obtaining catmint oil from *Nepeta cataria* by (a) contacting *Nepeta cataria* plant material with steam in a direct fired retort under vacuum to form a volatilized mixture comprising catmint oil and water; (b) condensing the volatilized mixture formed in step (a) to form a liquid mixture comprising catmint oil and water; (c) separating the liquid mixture formed in step (b) into a catmint oil phase and a water phase; and (d) recovering the catmint oil phase.

In further embodiments, this invention relates to a process for hydrogenating a catmint oil that has been obtained from plant material according to a process as described above, and incorporating the hydrogenated catmint oil into a formulation suitable for application to the skin, hair, fur, feathers or hide of a human or domesticated animal.

DETAILED DESCRIPTION

This invention provides improved processes for steam distilling plant material from *Nepeta cataria*, thereby achieving a greater yield of the essential oil thereof, herein referred to as catmint oil ("CMO").

Catmint oil from *N. cataria* is comprised predominantly of trans-cis and/or cis-trans isomers of nepetalactone, but also may comprise extraneous components including unsaturated components such as caryophyllenes, carvones, limonenes and other sesquiterpenes, and other unidentified impurities. CMO can be hydrogenated to prepare hydrogenated CMO, which contains dihydronepetalactone.

Catmint oil exhibits several characteristics that lead to low recovery of the oil from plant material using standard steam distillation techniques commonly employed for the isolation of essential oils from plant material. Catmint oil has significant solubility in water, and does not readily coalesce to form a separate oil phase from the condensed water used in the steam distillation process. Additionally, nepetalactone, the principal constituent of catmint oil, hydrates at high temperatures to non-volatile and unwanted side products. The present invention overcomes these disadvantages of the isolation of catmint oil from plant material to provide an economical method for recovering the oil in high yield at moderate temperatures.

In one embodiment of the invention, the solubility of catmint oil in water is reduced by the addition of salt to the aqueous phase during the distillation process. As a result, the amount of catmint oil in the wastewater leaving the process is reduced, resulting in a greater yield of catmint oil. The use of a salt to reduce the solubility of catmint oil in water has a further advantage in that it allows the oil to be less dense than the water phase. This allows the use of traditional oil collection equipment, wherein the catmint. oil is collected as an upper phase, which can easily be recovered by decantation. An additional advantage is that the rate at which the oil coalesces may be increased through the use of various salts.

According to conventional distillation processes for recovering catmint oil, plant material from *N. cataria* (herein also called catmint plant material) is contacted with steam to form a vapor phase heterogeneous mixture comprising predominantly catmint oil and water. This mixture is then condensed to form a heterogeneous liquid condensed mixture comprising a catmint oil phase and a water phase, and the catmint oil phase is recovered from this mixture.

Figure 1:
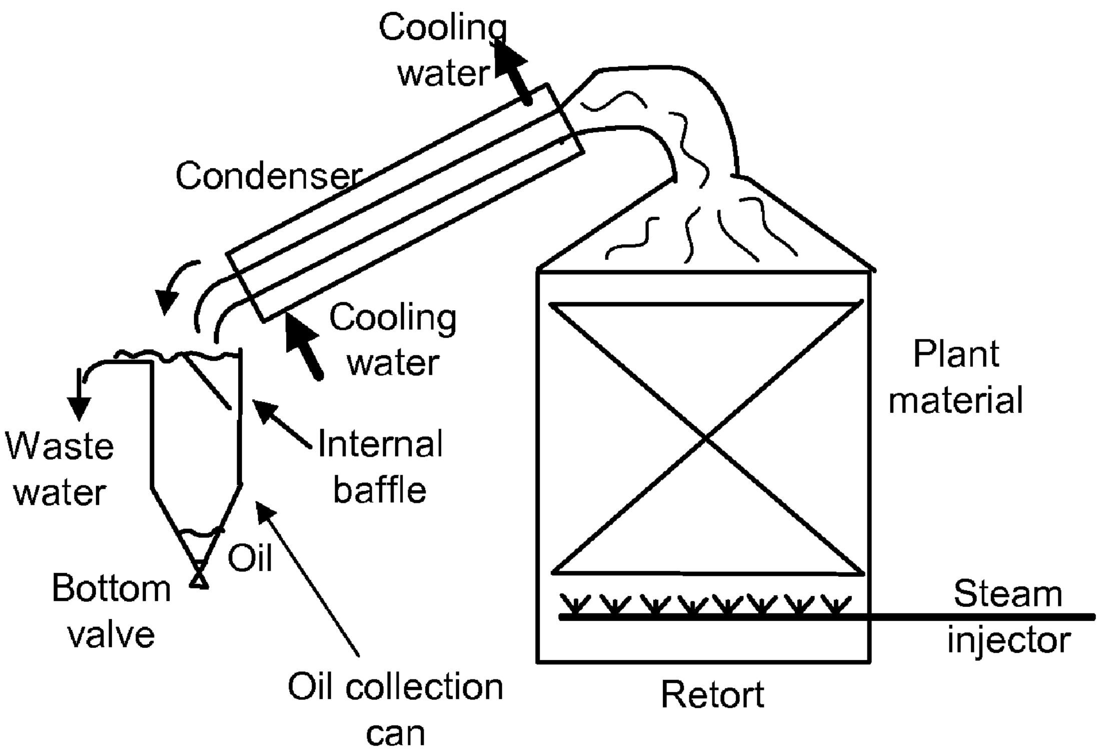
FIG. 1 shows an indirect fired traditional steam distillation apparatus for oils that are heavier or more dense than water.

A traditional steam distillation apparatus is shown schematically in FIG. 1. Plant material is packed into a retort over a set of steam injectors, a suitable retort that may be used for such purpose being that which is available from Juniper Mfg. (Redmond, Oreg.). The lid of the retort is closed and sealed to both the retort and to a condenser. Steam is injected through the injection manifold (or steam injector) and into the packed plant material. The steam provides two functions: 1) energy to disrupt the glandular (or secretory) trichomes on the plant and release the oil, and 2) formation of a heteroazeotrope with the oil and thus volatizes it sufficiently as to allow it to be transported into the vapor phase. The steam and volatized oil are ducted to a condenser.

Cooling water, from any suitable water source, flows through the condenser. Its cooling effect allows the steam and catmint oil vapor to condense. The condenser is configured in such a way as to allow gravity to drain the condensed water and catmint oil out of the condenser and into a collection can. The water and catmint oil are ducted into the collection can optionally using internal baffles in such a way as to produce a quiescent zone to allow the oil and water to effectively separate. The quiescent zone is the zone where the superficial velocity of the condensate is less than the disengagement velocity of the oil from the water.

Essential oils that are produced in large commercial quantities, i.e. spearmint and peppermint oils, are generally less dense than water, and when using a standard collection can, these essential oils would form a phase above the water. Catmint oil, however, is heavier (more dense) than water, and thus conventional collection equipment does not offer the same advantage in the case of catmint oil. As shown in FIG. 1, the water forms an aqueous phase above the heavier catmint oil. The water is thus generally removed as wastewater, for example by decantation. Typically, the temperature of the condensate is controlled at a modest temperature, approximately 40-60° C., to allow the oil and water to effectively separate in the quiescent zone of the separation can.

The use of a steam distillation apparatus similar to that shown in FIG. 1 in a conventional distillation process may be illustrated as follows: A glass resin kettle (as the retort) is outfitted with a steam injector plate, a condenser head and a graduated cylinder attached to the condenser as a simple collection can. The graduated cylinder is sized to have a condensate residence time of 20 to 30 minutes. Dried catmint plant material (100 grams) is packed into the resin kettle above the steam injector. The resin kettle is sealed and made leak tight. Live saturated steam is injected into the bottom of the resin kettle at a rate of approximately 40 g/min of steam per Kg of dried catmint plant material. The pressure of the steam is slightly above atmospheric pressure to allow for a pressure drop across the plant material and the condenser. The cooling water flow is adjusted to the condenser so that the condensate temperature is about 50° C. After the graduated cylinder is filled, with condensate, it overflows into a wastewater drain.

The still is operated in this fashion for 4.5 hours. Dichloromethane is added to the graduated cylinder. The resulting mixture of solvent and oil is removed. from the graduated cylinder and a portion is analyzed by GC. The GC analysis provides a measure of the total amount of oil collected in the cylinder without having to weigh the sample. The oil collected in the receiver is expected to be less than 0.15 wt. % of the original dry weight of the catmint plant material.

One aspect of this invention relates to the discovery that, after contacting the catmint plant material with steam, and cooling the volatilized mixture comprising catmint oil and water to form a heterogeneous condensed mixture, the catmint oil can be separated from the heterogeneous condensed mixture in greater yield than observed with conventional distillation techniques by contacting the condensed mixture with a salt that decreases the solubility of catmint oil in water. In a preferred embodiment, the salt will also increase the rate at which the oil coalesces and disengages from the aqueous phase, thus reducing oil loss as fine droplets in the aqueous phase.

More specifically, one embodiment of the processes hereof provides a process for obtaining catmint oil from *Nepeta cataria* by (a) contacting *Nepeta cataria* plant material with steam to form a volatilized mixture comprising catmint oil and water; (b) condensing the volatilized mixture formed in step (a) to form a liquid mixture comprising catmint oil and water in which catmint oil is dissolved in water; (c) contacting the liquid mixture formed in step (b) with salt to provide a mixture in which catmint oil and salt are both dissolved in water, and in which (i) the solubility of catmint oil in the solution of water and salt is at least about 50% less than the solubility of catmint oil in water, and/or (ii) the ratio $[(\rho_{catmint\ oil}-\rho_{aqueous\ solution})/\mu_{aqueous\ solution}]$, where $\rho$ is density, $\mu$ is viscosity and the aqueous solution is the solution of water and salt, is less than or equal to about −0.05, to provide in the mixture a catmint oil phase that is separated from an aqueous salt solution phase; and (d) recovering the catmint oil phase.

Figure 2:
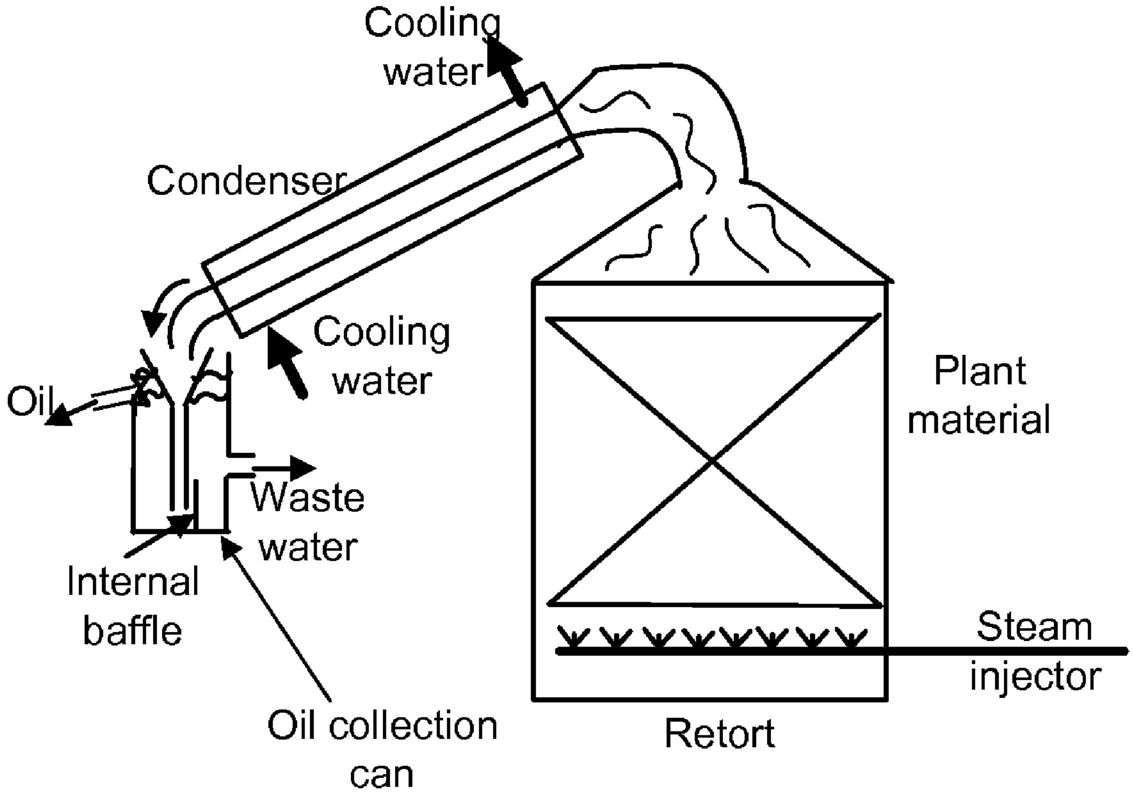
FIG. 2 shows an indirected fired steam distillation apparatus for oils that are lighter or less dense than water solutions.

This process can be carried out in a distillation apparatus as shown in FIG. 2. Plant material is packed into a retort. The lid of the retort is closed and sealed to both the retort and to a condenser. Steam for the distillation of the catmint plant material can be provided by any suitable means such as by direct injection through an injection manifold as illustrated in FIG. 2. In an alternative embodiment, the steam can be obtained by adding water to the retort, and boiling the water in the presence of the plant material. The latter method is referred to as using a direct fired retort.

The volatized oil that is produced when steam contacts the plant material is ducted, along with the steam, to a condenser. Cooling water, from any suitable water source, flows through the condenser. Its cooling effect allows the steam and catmint oil vapor to condense to form the heterogeneous liquid condensed mixture. The condenser is configured in such a way as to allow gravity to drain the condensed water and catmint oil out of the condenser and into a collection can. The water and catmint oil are ducted into the collection can, optionally using internal baffles in such a way as to produce a quiescent zone to allow the oil and water to effectively separate. Typically, the temperature of the condensate is controlled at a modest temperature, approximately 40-60° C., to allow the oil and water to effectively separate in the quiescent zone of the separation can.

The heterogeneous liquid condensed mixture comprising catmint oil and water can be contacted with salt by any suitable means, and it is preferable that the entire mixture comes into contact with salt. In one embodiment of the processes hereof, a porous material, such as burlap, filter paper, filter cloth (e.g. cheesecloth), or a fine mesh screen, is placed in a funnel, and the salt is placed on the porous material. The mixture catmint oil and water contacts the salt, and flows through the funnel into the collection can. In an alternative embodiment, the chosen salt can be preloaded in the collection can to allow the aqueous CMO mixture to directly contact the chosen salt. In yet another embodiment, a concentrated salt solution may be used, and the aqueous CMO mixture is brought into contact with the concentrated salt solution. For steam distillation systems described below wherein vacuum is used, the contacting of the aqueous CMO mixture with salt would be carried out in. a closed system.

In addition to its effects on solubility, the addition of salt to the aqueous CMO mixture also increases the disengagement rate of catmint oil from water. At a particular temperature, the ratio of the difference in the density (ρ) of catmint oil (CMO) and the density of the aqueous solution (aq. sol.) to the viscosity (μ) of the aqueous solution $[(\rho_{CMO}-\rho_{aq.\ sol.})/\mu_{aq.\ sol}]$ is indicative of the ease for disengaging oil droplets from the water. In the above ratio, the aqueous solution is water with or without salt, as the case may be. This ratio can be modified through the addition of salt to the water since the added salt changes both the water density and viscosity. The ratio can also be modified by changing the temperature of the mixture; temperatures of from about room temperature (about 25° C.) to about 75° C. are preferred, and temperatures of about 40° C. to about 60° C. are more preferred.

It is expected that the wastewater from the steam distillation process can be used as a fertilizer, and thus preferred salts include the sulfate, nitrate and phosphate salts of Groups 1 and 2 of the Periodic Table of the Elements.

By modifying the water density and viscosity, the position of the catmint oil layer in the collection can may be modified. Using conventional distillation techniques without salt addition, the catmint oil would be recovered as the bottom layer in the collecting can. By modifying the water density and viscosity, the catmint oil can be recovered from the top of the collecting can (for example, by decantation of the catmint oil phase), thereby allowing the use of conventional collecting equipment. In addition, corrosion products that may be formed in the condenser or collection can collect at the bottom of the collecting can, contaminating the liquid phase that is at the bottom of the can. Therefore, an additional advantage to having the oil phase as the top phase is that it is separated from any corrosion products that may be present.

Steam distillation of catmint oil according to a process of this invention may be carried out in a distillation apparatus as shown in as FIG. 2, and may be illustrated as follows: The distillation apparatus includes a retort (available from Juniper Mfg. (Redmond, Oreg.) with a steam injector plate, a condenser, and a conical collection can optionally with internal baffling in the collection can. The collection can is sized to have a condensate residence time of about 30 minutes. This residence time is high enough to provide a quiescent zone for the oil droplets to coalescence into a single continuous phase. This will occur when the superficial velocity of the water in the collection can is less than the settling velocities of the catmint oil droplets suspended in the water phase.

The distillation apparatus is modified such that the incoming catmint oil distillate is passed through a bed of a salt such as Epsom salts (hydrated magnesium sulfate) before entering the can. This is done by plugging the inlet funnel of the collection can with a piece of burlap to retain undissolved salt. The salt is dissolved by the incoming condensate stream, thus yielding a nearly salt-saturated water solution entering the can. Salt is replenished manually during the course of the run to maintain the presence of undissolved salt at all times.

Dried catmint plant material (13 kg) is packed into the retort above the steam injector so that the retort is full and the plant material is sealed securely to the sides of the retort so that channeling of the steam along the inside walls of the retort is minimized. The retort is sealed and made leak tight. Live steam produced in a separate boiler is injected into the bottom of the retort at a rate of 480 g/min for a total of 60 minutes. The pressure of the steam is slightly above atmospheric pressure to allow for pressure drop across the plant material and the condenser. The cooling water flow is adjusted to the condenser so that the condensate temperature is between 45° C. and 55° C. during the distillation. After the collection can is filled with condensate, the water phase condensate is drawn off the bottom of the collection can into a wastewater drain.

The still is operated in this fashion for 1 hour. A total of approximately 2.2 Kg of steam is used per Kg of dried catmint plant material. Approximately 50 mL or 52 grams of catmint oil is collected in the bottom of the collection can. This corresponds to approximately 0.40 wt % of the original dry weight of the catmint plant. The water effluent coming out is collected and later analyzed for dissolved oil by GC analysis. The GC analysis is expected to indicate an oil content of about 0.05 wt % of catmint oil in this water. This lower solubility corresponds to a yield improvement of 0.22 wt % of catmint oil relative to the dried plant weight. There is an additional yield gain of about 0.06 wt % of oil relative to the dried plant weight due to improved disengagement of the oil from the water.

The loss of catmint oil to wastewater can be reduced by reducing the amount of water used during the distillation process. It has thus been found, in another embodiment hereof, that, in direct fired retorts, the amount of water used in the process can be reduced by recycling the water after it is condensed. Thus, by modifying the conventional distillation apparatus such that water flows from the collection can back to the retort (see FIG. 3), the amount of water used in the process can be reduced.

More specifically, the processes hereof further provide a process for obtaining catmint oil from *Nepeta cataria* by (a) contacting *Nepeta cataria* plant material with steam in a direct fired retort to form a volatilized mixture comprising catmint oil and water; (b) condensing the volatilized mixture formed in step (a) to form a liquid mixture comprising catmint oil and water; (c) separating the liquid mixture formed in step (b) into a catmint oil phase and a water phase; (d) recycling the water phase back to the direct fired retort of step (a); and (e) recovering the catmint oil phase.

The placement of the line that directs water from the collection can to the retort will depend on the position of the water in the collection can, i.e. whether the water phase is on top of the catmint oil or below the catmint oil. Water recycle from the collection can to the retort will function in distillation systems where no salt is used, but will also function in those distillation systems where salt is used to alter catmint oil solubility or the disengagement rate from water.

In a further embodiment of the processes hereof, the rate of hydrolysis of catmint oil to undesirable by-products (such as nepetalic acid) during the steam distillation process may be reduced.

Figure 3:
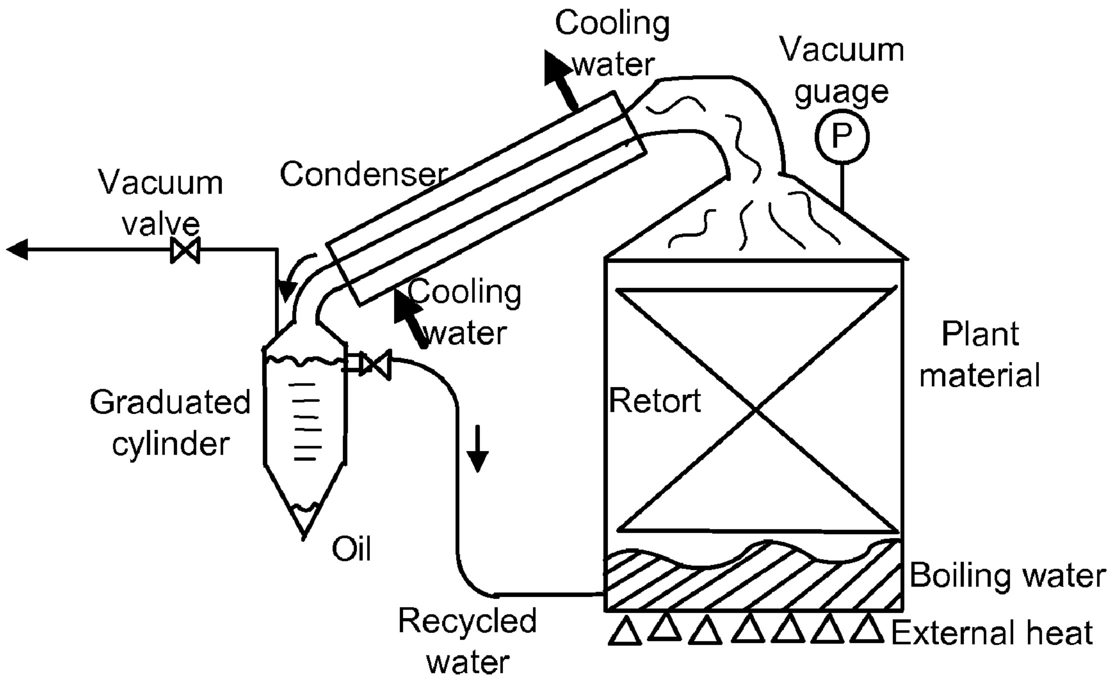
FIG. 3 shows a direct fired steam distillation apparatus connected to a vacuum system, with a means to recycle water for oils that are heavier or more dense than water.

It has been found that, at higher temperatures, nepetalactone isomers in catmint oil hydrate to undesirable products (such as nepetalic acid), and that the rate of formation of nepetalic acid increases with increasing temperature. Performing the distillation of catmint plant material at a lower temperature, such as a temperature of from about room temperature (about 25° C.) to about 75° C., preferably about 40° C. to about 60° C., will thus reduce the tendency for the hydration of nepetalactone to occur. The temperature can be reduced by operating the distillation apparatus under vacuum; and an example of such a system is shown in FIG. 3.

The amount of vacuum applied to the system will depend on the system components, however achieving an absolute pressure of about 13 kPa to about 70 kPa is preferred. An absolute pressure of about 20 kPa to about 45 kPa is more preferred. The application of vacuum can be used in distillation systems where no salt is used, but will also function in those distillation systems where salt is used to alter catmint oil solubility or the disengagement rate from water. In addition, the application of vacuum can be used in systems where water is recycled from the collection can back to the retort.

The advantageous attributes and effects of the processes hereof may be seen in a series of examples, as described below. The embodiments of these processes on which the examples are based are representative only, and the selection of those embodiments to illustrate the invention does not indicate that materials, conditions, arrangements, components, reactants, techniques or configurations not described in these examples are not suitable for practicing these processes, or that subject matter not described in these examples is excluded from the scope of the appended claims and equivalents thereof.

EXAMPLES

The following abbreviations are used: GC is gas chromatograph(y); GC-MS is gas chromatography-mass spectrometry; FID is flame ionization detector; NMR is nuclear magnetic resonance; C is Centigrade, MPa is mega Pascal; kPa is kilo Pascal; h is hour; ° C. is degrees Centigrade; Kg is kilogram; g is gram; min is minute; aq.sol is aqueous solution; wt. % is weight percent.

Epsom salt (heptahydrate) was purchased at Pathmark Stores Inc., Newark Del. Calcium nitrate tetrahydrate, magnesium sulfate, potassium nitrate, and urea were obtained from Sigma-Aldrich (St. Louis, Mo.). Plant material was grown in a greenhouse using Johnny's catmint seed (Winslow, Me.).

Determination of Catmint Oil Constituents and the Hydrogenated Compounds Thereof:

Samples were diluted with an. internal standard solution and injected on a DB FFAP column using an HP5890 GC equipped with a FID detector (Agilent Technologies, Palo Alto, Calif.). The injection and detector temperatures were 250° C. The temperature of the column was linearly ramped from 50° C. to 250° C. for 20 min and held at 250° C. for the duration of the run. A split mode inlet was used. Peak identification and relative response factors of the major components were determined using calibration standards of nepetalactone and nepetalic acid.

Example 1

Effect of Salt on the Solubility of Catmint Oil (CMO) in Water

Mixtures of CMO with water, and with various solutions of salt in water, were equilibrated and the aqueous phase was analyzed by GC to measure CMO concentration (Table 1). A sample of CMO in pure water was used as control and yielded a solubility of 0.15 weight percent. Upon addition of salt, the catmint oil phase floated on top of the aqueous phase at equilibrium for most compositions. GC analysis revealed that the CMO solubility in the water was dependent on the type of salt used. In general, the CMO concentration in water decreased with increasing salt content except for urea. In addition, CMO solubility was significantly reduced in $MgSO_4$ solutions relative to other salt solutions.

TABLE 1

Solubility of catmint oil in various aqueous salt solutions at room temperature.

| Sample Number | Salt | Salt (wt %) | CMO phase | CMO in aqueous phase (wt %) |
|---|---|---|---|---|
| 1 | $Ca(NO_3)_2$ | 5 | bottom | 0.26 |
| 2 | $Ca(NO_3)_2$ | 10 | top | 0.19 |
| 3 | $Ca(NO_3)_2$ | 15 | top | 0.16 |
| 4 | $Ca(NO_3)_2$ | 20 | top | 0.15 |
| 5 | $MgSO_4$ | 5 | top | 0.11 |
| 6 | $MgSO_4$ | 10 | top | 0.07 |
| 7 | $MgSO_4$ | 15 | top | 0.05 |
| 8 | $MgSO_4$ | 20 | top | 0.04 |
| 9 | Urea | 5 | bottom | 0.24 |
| 10 | Urea | 10 | bottom | 0.26 |
| 11 | Urea | 15 | top | 0.31 |
| 12 | Urea | 20 | top | 0.34 |
| 13 | $KNO_3$ | 5 | bottom | 0.21 |
| 14 | $KNO_3$ | 10 | top | 0.18 |
| 15 | $KNO_3$ | 15 | top | 0.14 |
| 16 | $KNO_3$ | 20 | top | 0.13 |

"CMO phase" refers to the position of the CMO as either below, the aqueous phase ("bottom"), or above the aqueous phase ("top").

Typical steam distillations use 1 to 4 Kg of water per Kg of dried plant material. Without salt addition, there is a yield loss of 0.11 to 0.88 wt % catmint oil based on dried plant weight. However, with magnesium sulfate salt addition [see Table 1], this yield loss decreased to 0.04 to 0.16 wt. % oil based on dried plant weight. This resulted in a yield increase of 0.07 to 0.72 wt. % catmint oil based on dried plant weight.

Example 2

Disengagement Rate of Catmint Oil from Water

Figure 4:
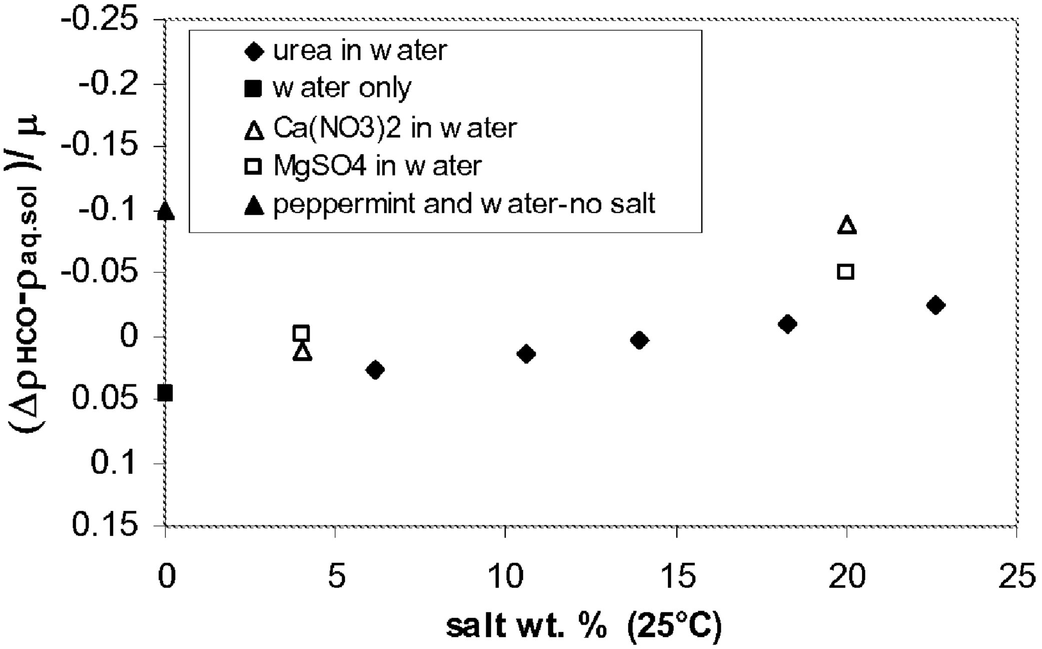
FIG. 4 is a plot of the ratio of the difference in density of catmint oil (CMO) and aqueous solution to the viscosity of the aqueous solution at 25° C.
Figure 4:
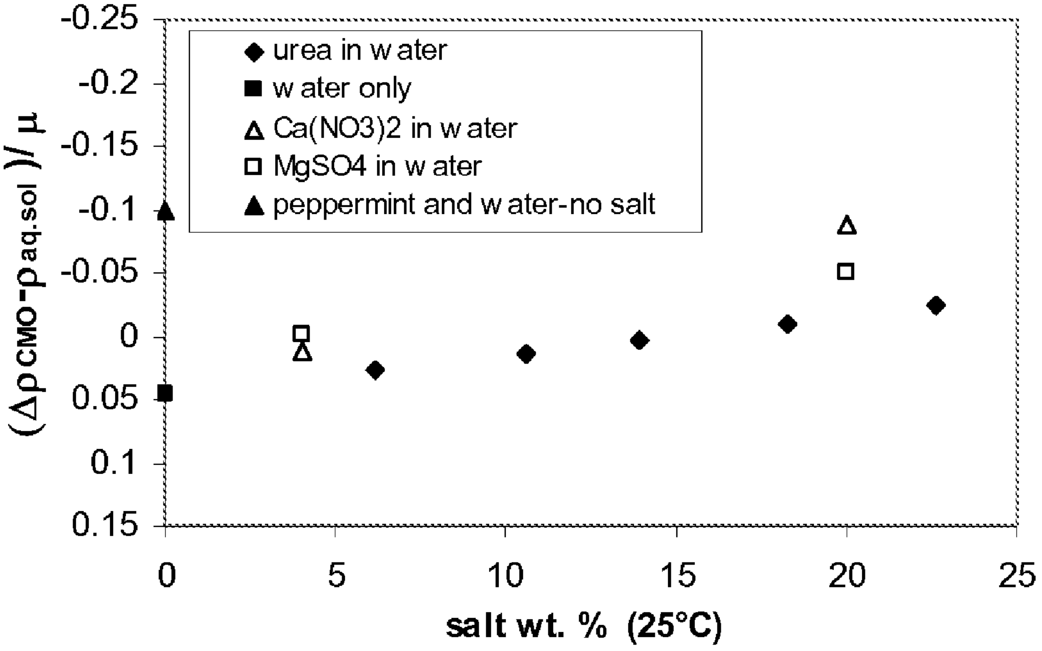
Figure 5:
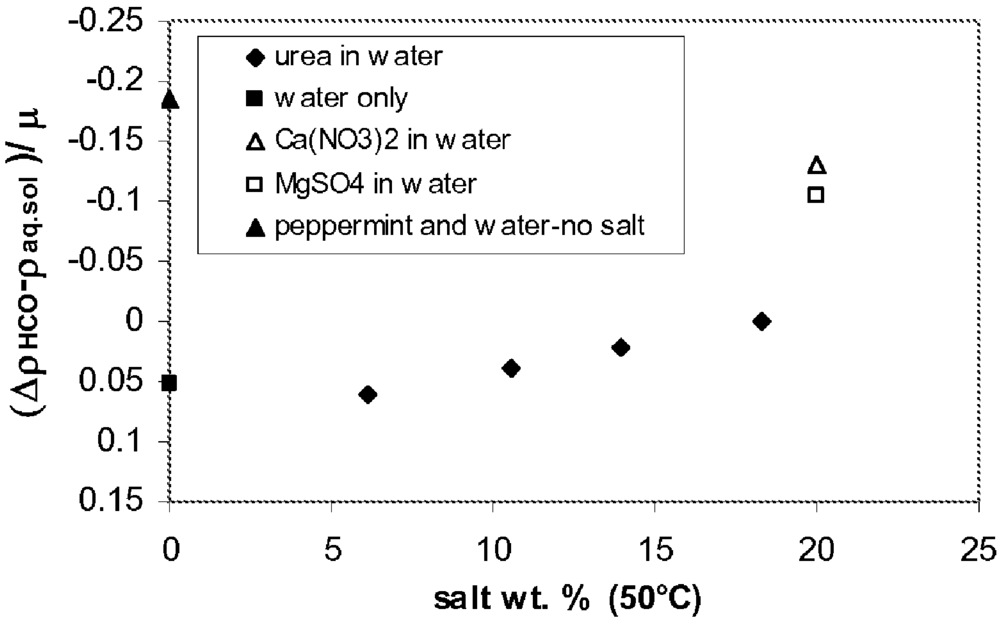
FIG. 5 is a plot of the ratio of the difference in density of catmint oil (CMO) and aqueous solution to the viscosity of aqueous solution at 50° C.
Figure 5:
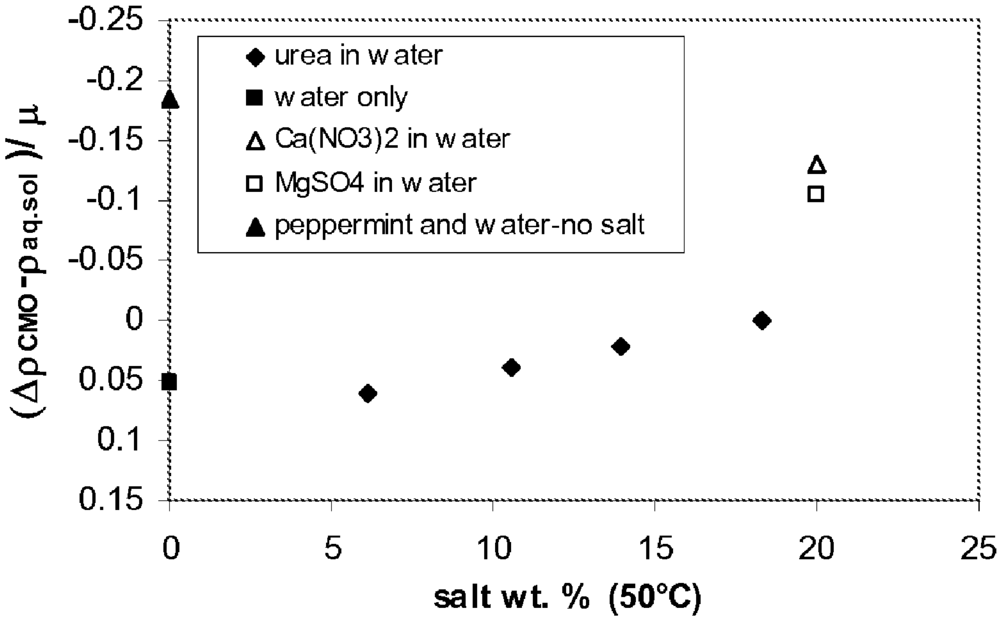

The ratio of the difference in density of catmint oil and aqueous solution (i.e. water with or without the addition of salt) to the viscosity of the aqueous solution $[(\rho_{CMO}-\rho_{aq.\ sol})/\mu_{aq.\ sol.}]$ (wherein "aq. sol." is the abbreviation for aqueous solution) was evaluated for mixtures of catmint oil and aqueous solutions at various temperatures. The density of catmint oil was measured using standard techniques. The density and viscosity of the salt solutions are available in the literature [*Perry's Chemical Engineers' Handbook,* 6$^{th}$ Edition, 1984; International Critical Tables of Numerical Data, Physics, Chemistry and Technology (1st Electronic Edition), Knovel Co., 2003]. The values for mixtures of water/catmint oil and various salt water solutions with catmint oil were plotted at 25° C. and 50° C. in FIGS. 4 and 5, respectively. A mixture of water and peppermint oil was used as a comparison.

The greater the extent to which the calculated ratios depart from zero, the faster will be the oil disengagement rate from the water or salt water solution. A negative ratio indicates that the catmint oil phase will be lighter than the aqueous phase. The oil will float on top of the water. A positive ratio indicates that the catmint oil is heavier than the water or salt water solution, and thus the oil will sink below the aqueous phase. Aqueous solutions of magnesium sulfate and calcium nitrate were particularly effective in improving the separation of catmint oil from the water. In addition, the addition of aqueous solutions of magnesium sulfate and calcium nitrate to the water made the water heavier than catmint oil, which permitted the collection of the distilled catmint oil as the top phase in the collecting can. A temperature of 50° C. is preferred over 25° C.

Example 3

Comparative Example

Steam Distillation without Salt Addition

Steam distillation of catmint oil was carried out in a distillation apparatus similar to that shown in FIG. 1 for a conventional steam distillation [retort available from Juniper Mfg. (Redmond, Oreg.)]. The distillation apparatus included a retort with a steam injector plate, a condenser, and a conical collection can, wherein said conical collection optionally had internal baffling. The collection can was sized to have a condensate residence time of about 30 minutes. This residence time was high enough to provide a quiescent zone for the oil droplets to coalesce into a single continuous phase.

Dried catmint plant material (13 Kg) was packed into the retort above the steam injector so that the retort was full and the plant material was sealed securely to the sides of the retort so that channeling of the steam along the inside walls of the retort was minimized. The retort was sealed and made leak tight. Live steam produced in a separate boiler (not shown in FIG. 1) was injected into the bottom of the retort at a rate of 480 g/min for a total of 60 minutes. The pressure of the steam was slightly above atmospheric pressure to allow for a pressure drop across the plant material and the condenser. The cooling water flow was adjusted to the condenser so that the condensate temperature was between about 45° C. and 55° C. during the distillation. After the collection can was filled with condensate, the condensate overflowed into a wastewater drain. The distillation apparatus was operated in this fashion for 1 hour. A total of approximately 2.2 Kg of steam was used per Kg of dried catmint plant material.

Approximately 15.6 mL (16.2 grams) of catmint oil was collected in the bottom of the collection can. This corresponds to approximately 0.12 wt % of the original dry weight of the catmint plant. The water effluent coming out was collected and later analyzed for dissolved oil by GC analysis. The GC analysis indicated an oil content of about 0.15 wt % of catmint oil in this water. This is near the solubility limit of the catmint oil in water and constitutes a substantial yield loss of 0.33 wt % of catmint oil relative to the dried plant weight. This yield loss does not include losses due to poor disengagement of the oil from the water.

Example 4

Steam Distillation of Catmint Plant Material

Effect of Recycling Water

A steam distillation apparatus similar to that shown in FIG. 1 is used. A glass resin kettle (as the retort) is outfitted with a steam injector plate, a condenser head and a graduated cylinder attached to the condenser as a simple collection can. The graduated cylinder is sized to have a condensate residence time of 20 to 30 minutes. The apparatus was modified from that shown in FIG. 1 to be able to directly boil water in the base of the retort and to be able to recycle the water back to the retort from the oil collector (FIG. 2). A 10 mL graduated cylinder was used as the condensate collector. Deionized water (500 grams) was loaded in the heal of the resin kettle. Dried catmint plant material (100 grams) was packed into the resin kettle above the water. Electrical heating mantels were used to supply heat directly to the water and to maintain the plant bed temperature sufficient to not allow excessive condensation of water in the plant material. The heat input was adjusted so that the condensation residence time in the 10 mL graduated cylinder was between 10 and 20 minutes. Cooling water was supplied to the condenser to allow the condensate temperature to be about 30° C. Water from the condenser was periodically drained back to the retort.

The distillation apparatus was operated in this fashion for about 4.5 hours. Dichloromethane was added to the graduated cylinder. The resulting mixture of solvent and oil was removed from the graduated cylinder and a portion was analyzed by GC. The GC analysis provided a measure of the total amount of oil collected in the cylinder without having to weigh the sample. The oil collected in the receiver was about 0.17 wt % of the original dry weight of the catmint plant material. This shows a yield increase of at least 13% relative to that observed when the experiment is performed without recycle.

Example 5

Vacuum Steam Distillation of Catmint Plant Material with Water Recycle

The steam distillation apparatus described in Example 4 was modified to allow vacuum operation of the retort and condenser (FIG. 3). A 10 mL graduated cylinder was used as the condensate collector. Deionized water (500 grams) was loaded in the heal of the resin kettle. Dried catmint material (84 grams) was packed into the resin kettle above the water. Electrical heating mantels were used to supply heat directly to the water and to maintain the plant bed temperature sufficient to not allow excessive condensation of water in the plant material. The vacuum was adjusted so that the retort was running at an absolute pressure of 31 kPa (4.5 psia) and a boiling temperature of about 70° C. The condensation residence time in the 10 mL graduated cylinder was between 10 and 20 minutes. Cooling water was supplied to the condenser to allow the condensate temperature to be about 30° C. Water from the condenser was periodically drained back to the retort.

This still was operated in this fashion for about 7 hours. Dichloromethane was added to the graduated cylinder. The resulting mixture of solvent and oil was removed from the graduated cylinder and a portion was analyzed by GC. The GC analysis provided a measure of the total amount of oil collected. in the cylinder without having to weigh the sample. The oil collected in the receiver was about 0.3 wt. % of the original dry weight of the catmint plant material. This shows a significant increase in yield at a lower temperature of distillation.

Where a range of numerical values is recited is herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. A process for obtaining catmint oil from *Nepeta cataria* comprising:

(a) contacting *Nepeta cataria* plant material with steam to form a volatilized mixture comprising catmint oil and water;

(b) condensing the volatilized mixture formed in step (a) to form a liquid mixture comprising catmint oil and water in which catmint oil is dissolved in water;

(c) contacting the liquid mixture formed in step (b) with a salt, selected from the group consisting of sulfate, nitrate and phosphate salts of the elements of Groups 1 and 2 of the Periodic Table of the Elements, to provide a mixture in which catmint oil and salt are both dissolved in water, and in which (i) the solubility of catmint oil in the solution of water and salt is at least about 50% less than the solubility of catmint oil in water, and/or (ii) the ratio $[(\rho_{catmint\ oil}-\rho_{aqueous\ solution})/\mu_{aqueous\ solution}]$, where ρ is density, μ is viscosity and the aqueous solution is the solution of water and salt, is less than or equal to about −0.05, to provide in the mixture a catmint oil phase that is separated from an aqueous salt solution phase; and (d) recovering the catmint oil phase from the mixture to provide a separated catmint oil phase and a remaining aqueous salt solution phase.

2. The process of claim 1 wherein the solubility of catmint oil in the solution of water and salt is at least about 50% less than the solubility of catmint oil in water.

3. The process of claim 1 wherein the ratio $[(\rho_{catmint\ oil}-\rho_{aqueous\ solution})/\mu_{aqueous\ solution}]$, where ρ is density, μ is viscosity and the aqueous solution is the solution of water and salt, is less than or equal to about −0.05.

4. The process of claim 1 wherein (i) the solubility of catmint oil in the solution of water and salt is at least about 50% less than the solubility of catmint oil in water, and (ii) the ratio $[(\rho_{catmint\ oil}-\rho_{aqueous\ solution})/\mu_{aqueous\ solution}]$, where ρ is density, μ is viscosity and the aqueous solution is the solution of water and salt, is less than or equal to about −0.05.

5. The process of claim 1 wherein the salt is selected from the group consisting of the sulfate salts of elements of Groups 1 and 2 of the Periodic Table of the Elements.

6. The process of claim 1 wherein the salt is selected from the group consisting of the nitrate salts of elements of Groups 1 and 2 of the Periodic Table of the Elements.

7. The process of claim 1 wherein the salt is selected from the group consisting of the phosphate salts of elements of Groups 1 and 2 of the Periodic Table of the Elements.

8. A process for obtaining catmint oil from *Nepeta cataria* comprising:

(a) contacting *Nepeta cataria* plant material with steam in a direct fired retort to form a volatilized mixture comprising catmint oil and water;

(b) condensing the volatilized mixture formed in step (a) to form a liquid mixture comprising catmint oil and water;

(c) contacting the liquid mixture formed in step (b) with a salt selected from the group consisting of the sulfate, nitrate and phosphate salts of elements of Groups 1 and 2 of the Periodic Table of the Elements;

(d) separating the liquid mixture into a catmint oil phase and a water salt-containing phase;

(e) recycling the water phase back to the direct fired retort of step (a); and (f) recovering the catmint oil phase.

9. The process of claim 8 wherein the salt is selected from the group consisting of the nitrate salts of elements of Groups 1 and 2 of the Periodic Table of the Elements.

10. The process of claim 8 wherein the salt is selected from the group consisting of the sulfate salts of elements of Groups 1 and 2 of the Periodic Table of the Elements.

11. The process of claim 8 wherein the salt is selected from the group consisting of the phosphate salts of elements of Groups 1 and 2 of the Periodic Table of the Elements.

12. A process for obtaining catmint oil from *Nepeta cataria* comprising:

(a) contacting *Nepeta cataria* plant material with steam in a direct fired retort under vacuum to form a volatilized mixture comprising catmint oil and water;

(b) condensing the volatilized mixture formed in step (a) to form a liquid mixture comprising catmint oil and water;

(c) contacting the liquid mixture formed in step (b) with a salt selected from the group consisting of the sulfate, nitrate and phosphate salts of elements of Groups 1 and 2 of the Periodic Table of the Elements;

(d) separating the liquid mixture into a catmint oil phase and a water salt-containing phase; and (e) recovering the catmint oil phase from the mixture to provide the separated catmint oil phase and a remaining water phase.

13. The process of claim 12 wherein plant material is contacted with steam under an absolute pressure of about 13 kPa to about 70 kPa.

14. The process of claim 12 wherein plant material is contacted with steam under an absolute pressure of about 20 kPa to about 45 kPa.

15. The process of claim 12 further comprising a step of recycling the water phase back to the direct fired retort of step (a).

16. The process of claim 12 wherein the salt is selected from the group consisting of the nitrate salts of elements of Groups 1 and 2 of the Periodic Table of the Elements.

17. The process of claim 12 wherein the salt is selected from the group consisting of the sulfate salts of elements of Groups 1 and 2 of the Periodic Table of the Elements.

18. The process of claim 12 wherein the salt is selected from the group consisting of the phosphate salts of elements of Groups 1 and 2 of the Periodic Table of the Elements.

* * * * *